United States Patent
Cai et al.

(10) Patent No.: US 11,708,604 B2
(45) Date of Patent: Jul. 25, 2023

(54) GENE SEQUENCING SUBSTRATE AND METHOD FOR MANUFACTURING THE SAME, GENE SEQUENCING DEVICE AND GENE SEQUENCING METHOD

(71) Applicants: BEIJING BOE OPTOELECTRONICS TECHNOLOGY CO., LTD., Beijing (CN); BOE TECHNOLOGY GROUP CO., LTD., Beijing (CN)

(72) Inventors: Peizhi Cai, Beijing (CN); Fengchun Pang, Beijing (CN); Yue Geng, Beijing (CN); Le Gu, Beijing (CN); Chuncheng Che, Beijing (CN)

(73) Assignees: BEIJING BOE OPTOELECTRONICS TECHNOLOGY CO., LTD., Beijing (CN); BOE TECHNOLOGY GROUP CO., LTD., Beijing (CN)

(*) Notice: Subject to any disclaimer, the term of this patent is extended or adjusted under 35 U.S.C. 154(b) by 781 days.

(21) Appl. No.: 16/486,038

(22) PCT Filed: Dec. 24, 2018

(86) PCT No.: PCT/CN2018/123109
§ 371 (c)(1),
(2) Date: Aug. 14, 2019

(87) PCT Pub. No.: WO2019/134547
PCT Pub. Date: Jul. 11, 2019

(65) Prior Publication Data
US 2020/0048698 A1 Feb. 13, 2020

(30) Foreign Application Priority Data
Jan. 3, 2018 (CN) .......................... 201810004294.3

(51) Int. Cl.
C12Q 1/68 (2018.01)
G03F 7/00 (2006.01)
C12Q 1/6869 (2018.01)

(52) U.S. Cl.
CPC .......... *C12Q 1/6869* (2013.01); *G03F 7/0002* (2013.01)

(58) Field of Classification Search
CPC .......................... C12Q 1/6869; G03F 7/0002
See application file for complete search history.

(56) References Cited

U.S. PATENT DOCUMENTS

2011/0254205 A1 10/2011 Inamiya et al.
2013/0324421 A1* 12/2013 Rothberg ........... G01N 27/4148
506/2

(Continued)

FOREIGN PATENT DOCUMENTS

CN 102165558 A 8/2011
CN 104073425 A 10/2014

(Continued)

OTHER PUBLICATIONS

Wu et al. The Royal Society of Chemistry 2011, Lab Chip, 11, pp. 2984-2989 . (Year: 2011).*

(Continued)

*Primary Examiner* — Jezia Riley
(74) *Attorney, Agent, or Firm* — Nath, Goldberg & Meyer; Joshua B. Goldberg

(57) ABSTRACT

A gene sequencing substrate and a method for manufacturing the same, and a gene sequencing device are provided. It belongs to the technical field of gene sequencing, and can solve the problem of high cost of the high-throughput sequencing chip in the prior art. The gene sequencing substrate of the present disclosure comprises a plastic material with concave structures as base substrate, and the (Continued)

concave structures serve as reaction cells. Since the base substrate has plasticity, the concave structures can be formed by a simple process to reduce the cost of the gene sequencing substrate. Meanwhile, a first protective layer may be provided on the inner wall of the concave structures for preventing the inner wall of the concave structures from being corroded by the reaction liquid.

9 Claims, 3 Drawing Sheets

(56) References Cited

U.S. PATENT DOCUMENTS

| | | | |
|---|---|---|---|
| 2018/0237846 A1 | 8/2018 | Geng et al. | |
| 2018/0266980 A1* | 9/2018 | Cicero | C12Q 1/6869 |
| 2018/0280981 A1* | 10/2018 | Tan | G01N 27/44791 |
| 2019/0025242 A1 | 1/2019 | Pang et al. | |
| 2019/0203289 A1 | 7/2019 | Pang et al. | |

FOREIGN PATENT DOCUMENTS

| | | | |
|---|---|---|---|
| CN | 106497774 A | | 3/2017 |
| CN | 106591109 A | | 4/2017 |
| CN | 106939284 A | | 7/2017 |
| CN | 107402199 A | | 11/2017 |
| CN | 108060069 A | * | 5/2018 |
| CN | 108220412 A | | 6/2018 |

OTHER PUBLICATIONS

First Office Action dated Jan. 15, 2020, for corresponding Chinese application 201810004294.3.

Hong-Xing, Y. et al., "Green Building Development and Applicant of Renewable Energy", China Railway Publishing House, Dec. 2016, pp. 146.

Darrin, M. et al, "Systems Engineering for Microscale and Nanoscale Technologies", National Defense Industry Press, Sep. 2015, pp. 123-124.

Bo-Rong, C. et al. "Integrated Optics", University of Electronic Technology Press, May 1990, pp. 260.

* cited by examiner (1) Coating the Base Substrate

Template for imprinting

Plastic polymer base substrate

Substrate (2) Heating and Pressing

Heating to a temperature above the glass transition temperature (3) Cooling for Separation

GENE SEQUENCING SUBSTRATE AND METHOD FOR MANUFACTURING THE SAME, GENE SEQUENCING DEVICE AND GENE SEQUENCING METHOD

CROSS REFERENCE TO THE RELATED APPLICATION

This is a National Phase Application filed under 35 U.S.C. 371 as a national stage of PCT/CN2018/123109, filed Dec. 24, 2018, an application claiming the benefit of Chinese Application No. 201810004294.3, filed Jan. 3, 2018, the content of each of which is hereby incorporated by reference in its entirety.

TECHNICAL FIELD

The present disclosure belongs to the technical field of gene sequencing, and particularly relates to a gene sequencing substrate and a method for manufacturing the same, a gene sequencing device and a gene sequencing method.

BACKGROUND TECHNOLOGY

Gene sequencing technology is the most commonly used technology in modern molecular biology research. The current predominant sequencing technology in the market is high-throughput sequencing technology.

High-throughput sequencing technology includes Illumina sequencing-synthesis technology, Thermo Fisher ion-semiconductor sequencing technology, sequencing by ligation technology, Roche pyrosequencing technology, and the like.

At present, the predominant second-generation chip for the high-throughput sequencing in the market is nano well sequencing chip.

There are at least the following problems in the present chip: as shown in FIG. 1, the existing sequencing chip has a substrate in which nano wells are directly formed on a glass base substrate. The process for forming nano wells on the rigid glass base substrate is complicated and costly, and is difficult to be accepted by ordinary consumers. Therefore, it is desired to develop a sequencing chip with a lower sequencing cost.

SUMMARY

To solve the high cost problem of the existing high-throughput sequencing chip, the present disclosure provides a gene sequencing substrate and a method for manufacturing the same, a gene sequencing device and a gene sequencing method.

The gene sequencing substrate according to the present disclosure comprises a plastic base substrate with a surface having concave structures.

The concave structures of the gene sequencing substrate can be used as reaction cells for gene sequencing.

Optionally, the plastic base substrate comprises any one selected from a group consisting of poly(methyl methacrylate) (PMMA), polydimethylsiloxane (PDMS), poly(ethylene terephthalate) (PET), polyimide, polyisoprene and combinations thereof.

Optionally, the concave structures have a depth of 10 nm to 100 µm.

Optionally, the gene sequencing substrate comprises a first protective layer disposed on the base substrate which at least covers the concave structures.

The first protective layer comprises transparent metal oxide(s) which is any one selected from a group consisting of indium tin oxide, indium zinc oxide, tantalum oxide and hafnium oxide.

The present disclosure further provides a method for manufacturing a gene sequencing substrate, comprising:
forming concave structures on a surface of a plastic base substrate.

The concave structures can be used as reaction cells for gene sequencing.

Optionally, forming concave structures on a surface of a plastic material comprises:
softening the plastic base substrate by heating;
forming the concave structures on the surface of the plastic base substrate by a nanoimprinting process; and
cooling the base substrate.

Optionally, forming concave structures on a surface of a plastic material comprises forming the concave structures by an exposure etching process.

The method for manufacturing a gene sequencing substrate according to the present disclosure further comprises forming a first protective layer on the base substrate which at least covers the concave structures.

The present disclosure further provides a gene sequencing device comprising a first substrate and a second substrate disposed opposite to each other, and the first substrate is the gene sequencing substrate described above.

Optionally, the second substrate has an inlet and an outlet.

Optionally, the second substrate has a micro flow channel which connects the concave structures with the inlet and outlet, and the micro flow channel has a second protective layer comprising metal oxide(s) on the inner wall thereof.

The present disclosure yet further provides a gene sequencing method comprising a step of performing gene sequencing using the above-described gene sequencing device.

DETAILED DESCRIPTION OF THE EMBODIMENTS

For a better understanding of the embodiments of the present disclosure, the present disclosure will be further described in detail below with reference to the accompanying drawings and specific embodiments.

Some embodiments of the present disclosure provide a gene sequencing substrate comprising a plastic base substrate which has a surface with concave structures thereon. The concave structures can be used as reaction cells for gene sequencing. The gene sequencing substrate may further comprise a first protective layer disposed on the base substrate which at least covers the concave structures, and the first protective layer has enough chemical resistance to a reagent for the gene sequencing and adhesivity with the plastic base substrate, so that results of the gene sequencing can be assured and the first protective layer would not shed off after the gene sequencing.

Figure 1:
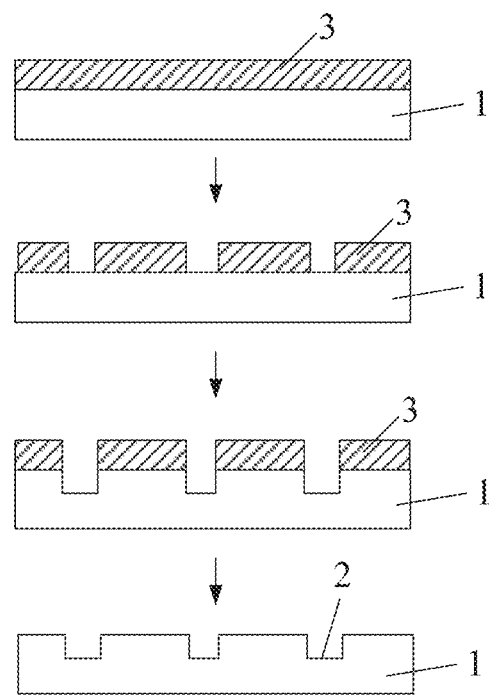
FIG. 1 is a schematic view showing a process of manufacturing a gene sequencing substrate in the prior art.
Figure 2:
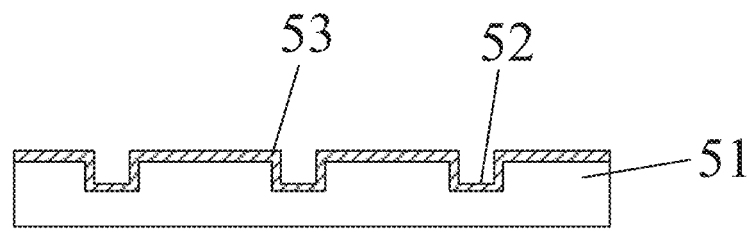
FIG. 2 is a schematic cross-sectional view of the gene sequencing substrate according to an embodiment of the present disclosure.

In one embodiment, as shown in FIG. 2, the gene sequencing substrate comprises a plastic base substrate 51 having a surface with concave structures 52 thereon. The concave structures 52 serve as reaction cells for gene sequencing. The term of "plastic base substrate" herein means that, when being subjected to an external force, the base substrate is significantly deformed but not destroyed. Since the base substrate 51 has plasticity, the concave structures 52 can be formed by a simple process, thereby ensuring the production efficiency of the gene sequencing substrate and reducing manufacturing costs. Further, a first protective layer 53 is provided on the base substrate to protect the surface of the concave structures 52 from being corroded by the reaction liquid.

Figure 3:
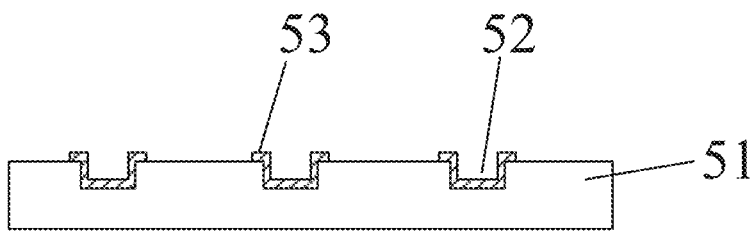
FIG. 3 is a schematic cross-sectional view of the gene sequencing substrate according to an embodiment of the present disclosure.
Figure 4:
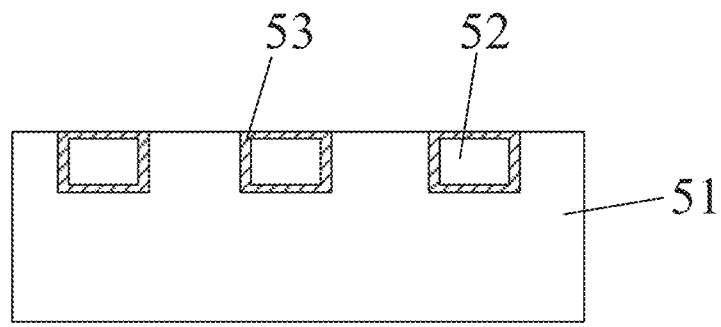
FIG. 4 is a top view of the gene sequencing substrate in FIG. 3.

In another embodiment, as shown in FIGS. 3 and 4, the gene sequencing substrate comprises a plastic base substrate 51 having a surface with concave structures 52 thereon. The concave structures 52 serve as reaction cells for gene sequencing. A first protective layer 53 is provided on the base substrate to at least cover the concave structures. In other words, the first protective layer 53 is disposed only on the base substrate at the position in contact with the reaction liquid, so as to save material.

The plastic base substrate used in the present disclosure comprises any one selected from a group consisting of poly(methyl methacrylate) (PMMA), polydimethylsiloxane (PDMS), poly(ethylene terephthalate) (PET), polyimide, polyisoprene and combinations thereof.

Compared with the rigid glass base substrate 1 in the prior art, the present disclosure uses a plastic polymer as the base substrate 51 which is easier for processing the concave structures 52 and thereby effectively reducing the cost.

In some embodiments of the present disclosure, the concave structures have a depth of 10 nm to 100 μm.

Each concave structure has a cross section which may be in a circular or square shape, etc. When the concave structure has a cross section in a circular shape, the circular shape has a diameter in the range of 10 nm to 100 μm. When the concave structure has a cross section in a square shape, the square shape has a length and a width in the range of 10 nm to 100 μm. If the size level of the concave structure is between 10 nm and 1000 nm, it is usually called nano-well; and if the size level of the concave structure is 1 μm to 100 μm, it is usually called micro-well.

In some embodiments of the present disclosure, the first protective layer is a transparent layer formed of transparent metal oxide(s) which is any one selected from a group consisting of indium tin oxide (ITO), indium zinc oxide (IZO), tantalum oxide (TaOx), hafnium oxide (HfOx) and combinations thereof.

It is to be understood that, in the drawings corresponding to the embodiments of the present disclosure, the size, thickness, and the like of each structural layers shown in the drawings are merely illustrative. In the actual process, the projected area of each structural layer on the base substrate may be the same or different. Meanwhile, the geometric shape of each layer is not limited to the structure shown in the drawings. For example, the geometric shape may be a rectangle as shown in the drawings, and may also be trapezoid or other shapes.

Figure 7:
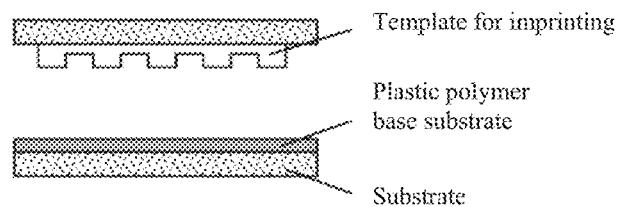
FIG. 7 is a flow chart of the method for manufacturing the gene sequencing substrate according to an embodiment of the present disclosure.
Figure 7:
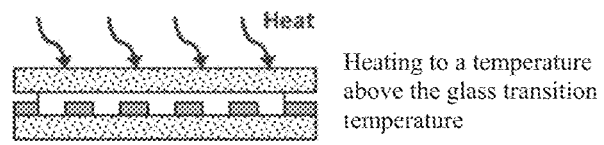
Figure 7:
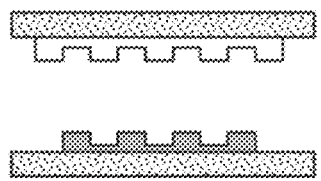

Further embodiments of the present disclosure provide a method for manufacturing a gene sequencing substrate comprising the following steps, as shown in FIG. 7:
  softening a plastic base substrate by heating;
  forming concave structures on a surface of the plastic base substrate by a nanoimprinting process; and
  cooling the plastic base substrate.

The plastic base substrate may be formed of any material selected from a group consisting of poly(methyl methacrylate) (PMMA), polydimethylsiloxane (PDMS), poly(ethylene terephthalate) (PET), polyimide, polyisoprene, and combinations thereof. The effect of the heating in this step is to soften the plastic base substrate, so that the surface of the plastic base substrate can be deformed in the subsequent step to form the concave structures. The specific heating temperature may be varied depending on the material forming the plastic base substrate. The specific heating temperature in the softening step depends on the glass transition temperature of the material forming the plastic base substrate. The plastic base substrate may be heated to a temperature T above the glass transition temperature Tgt ($T<Tgt+10°$ C.), which results in a reduced viscosity and an improved fluidity of the polymer during imprinting. Moreover, in this temperature range, the movement of macromolecular segments can be fully carried out in the polymer, so that the polymer could be in the elastomeric state and deform under a certain pressure.

The concave structures are formed directly on the surface of the plastic base substrate by a nanoimprinting process, and the concave structures are used as the reaction cells for gene sequencing;

In nanoimprinting, a rigid template with nano-patterns is adopted to imprint a pattern at nano level on the surface of the plastic material. The pressure applied during nanoimprinting may be 1 to 40 bar.

Nanoimprinting can produce nano patterns repeatedly on the surface of a large plastic material in large quantity, and the resulting patterns have fairly good uniformity and repeatability. The above method for forming the concave structures has advantages of extremely low cost, simplicity and high efficiency.

Optionally, in order to increase the corrosion resistance of the gene sequencing substrate, the method for manufacturing the gene sequencing substrate of the present disclosure further comprises forming a first protective layer on the base substrate which at least covers the concave structures.

Specifically, the first protective layer may be an entire protective layer that completely covers the surface of the plastic base substrate, or may be a partial protective layer disposed only at the position in contact with the reaction liquid during gene sequencing. The first protective layer may be a metal oxide protective layer, and the metal oxide may be a transparent metal oxide such as indium tin oxide, indium zinc oxide, tantalum oxide, hafnium oxide or the like.

A person skilled in the art can reasonably select a method for forming the first protective layer according to the material of the first protective layer. For example, when a metal oxide is used to form the first protective layer, the first protective layer may be formed by sputtering and vapor plating.

Further embodiments of the present disclosure provide another method for manufacturing the gene sequencing substrate, which is similar to the above-described manufacturing method except that an exposure etching process is employed in this method to form the concave structures on the surface of the plastic base substrate.

In the present embodiment, micro-wells of 1 μm to 100 μm are formed on the surface of the plastic base substrate by an exposure etching process, and the micro-well has a similar structure to that of the nano-wells according to the above embodiment of the present disclosure. Although the sequencing capacity of the micro-well is slightly lower than that of the nano-well, the sequencing principle is the same. Meanwhile, the micro-well of the embodiment can be formed at a lower cost, and can be manufactured in mass production.

Further embodiments of the present disclosure provide a gene sequencing device comprising a first substrate and a second substrate disposed opposite to each other, wherein the first substrate is the gene sequencing substrate described above.

Figure 5:
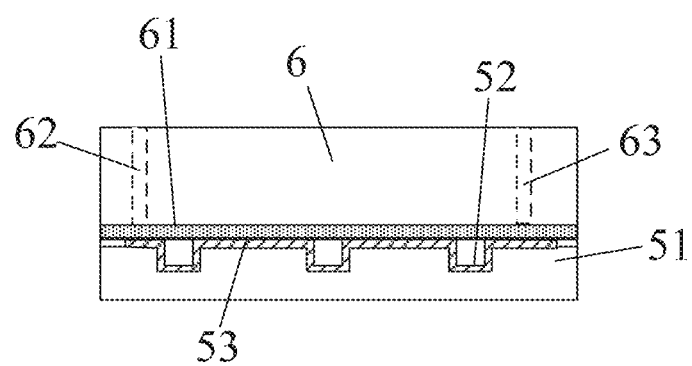
FIG. 5 is a schematic cross-sectional view of the gene sequencing device according to an embodiment of the present disclosure.
Figure 6:
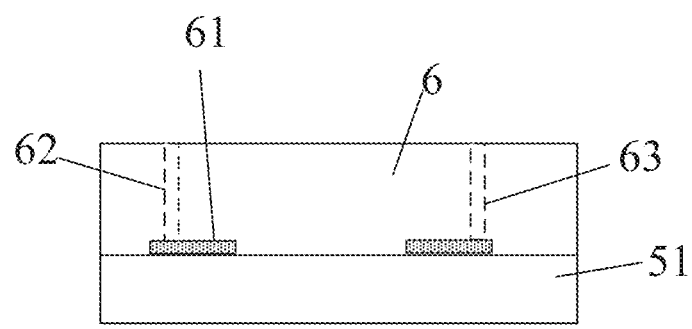
FIG. 6 is a schematic side view of the gene sequencing device in FIG. 5.

FIG. 5 is a schematic cross-sectional view of the gene sequencing device according to an embodiment of the present disclosure, and FIG. 6 is a schematic side view of the gene sequencing device according to this embodiment. As shown in FIG. 5, the second substrate 6 is disposed above the first substrate comprising the plastic base substrate 51 and the first protective layer 53 provided on the base substrate, wherein the base substrate has a surface with concave structures 52; and the second substrate 6 is provided with the inlet 62, the outlet 63 and the micro flow channel 61 for connecting the concave structures 52 with either the inlet 62 or the outlet 63. A second protective layer may be disposed on the inner wall of the micro flow channel 61.

The inlet 62 is used to add various reagents for gene sequencing, and the outlet 63 is used to discharge various waste liquids and reagents. It should be noted that the shape of the inlet 62 and the outlet 63 of the present disclosure is not limited to the shape shown in FIG. 5 and the shape and size of the inlet 62 and the outlet 63 may be varied depending on actual conditions.

Some embodiments of the present disclosure provide a method for gene sequencing comprising a step of performing gene sequencing using the gene sequencing device.

The detection of liquid samples is realized by integrating the reaction cell, the micro flow channel 61, the inlet 62 and the outlet 63, the biochemical reaction unit (not shown), or other required functional units on the first substrate and the second substrate 6 to form the gene sequencing device of the present embodiment. The gene sequencing device has a significantly high integration degree, and the size of the reaction cell may be at a micrometer level or a nanometer level, therefore requiring a very small amount of the test samples and reagents. The detection has a fast reaction speed, which is convenient for high-throughput testing and the like.

Example 1

In this example, the method for manufacturing the gene sequencing substrate of the present disclosure is set forth in detail, in which the plastic base substrate is formed by poly(methyl methacrylate) (PMMA).

1. Coating PMMA raw material on a substrate with a thickness of 500 nm to form the PMMA plastic base substrate;
2. Heating the plastic base substrate to a temperature T above its glass transition temperature (T<Tgt+10° C.);

Since PMMA has a glass transition temperature of about 100° C., the plastic base substrate may be heated to 105° C.;

3. Applying a pressure of 25 bar to the heated plastic base substrate by using a patterned template, to form the concave structures corresponding to the template on the plastic base substrate under the action of the template;
4. Cooling the plastic base substrate and the template to a temperature (usually room temperature) below the glass transition temperature of the plastic base substrate, to make the plastic base substrate be cured; and
5. Removing the template to obtain the plastic base substrate with the concave structures.

It can be understood that the foregoing embodiments are merely illustrative embodiments employed for describing the principle of the present invention. However, the present invention is not limited thereto. For a person of ordinary skill in the art, various deformations and improvements can be made without departing from the spirit and essence of the present invention. These deformations and modifications shall fall into the protection scope of the present invention.

The invention claimed is:

1. A gene sequencing substrate comprising a plastic base substrate with a surface having concave structures, wherein the gene sequencing substrate further comprises a first protective layer disposed on the plastic base substrate which at least covers the concave structures, and the first protective layer has enough chemical resistance to a reagent for the gene sequencing and adhesivity with the plastic base substrate.

2. The gene sequencing substrate according to claim 1, wherein the plastic base substrate comprises any one selected from a group consisting of poly(methyl methacrylate), polydimethylsiloxane, poly(ethylene terephthalate), polyimide, polyisoprene, and combinations thereof.

3. The gene sequencing substrate according to claim 1, wherein the concave structures have a depth of 10 nm to 100 μm.

4. The gene sequencing substrate according to claim 1, wherein the first protective layer comprises any transparent metal oxide selected from a group consisting of indium tin oxide, indium zinc oxide, tantalum oxide, hafnium oxide and combinations thereof.

5. A method for manufacturing the gene sequencing substrate according to claim 1, comprising:
    forming the concave structures on a surface of the plastic base substrate, and
    forming a first protective layer on the plastic base substrate, wherein the first protective layer at least covers the concave structures.

6. The method for manufacturing the gene sequencing substrate according to claim 5, wherein forming the concave structures on a surface of the plastic base substrate comprises:
    softening the plastic base substrate by heating;
    forming the concave structures on a surface of the plastic base substrate by a nanoimprinting process; and
    cooling the plastic base substrate with the concave structures.

7. The method for manufacturing the gene sequencing substrate according to claim 5, wherein forming the concave structures on a surface of the plastic base substrate comprises forming the concave structures by an exposure etching process.

8. A gene sequencing device, comprising a first substrate and a second substrate disposed opposite to each other, wherein the first substrate is the gene sequencing substrate according to claim 1, and the second substrate is provided with an inlet and an outlet.

9. The gene sequencing device according to claim 8, wherein the second substrate is provided with a micro flow channel which connects the concave structures with either the inlet or the outlet, and the inner wall of the micro flow channel is provided with a second protective layer formed of a metal oxide.

* * * * *